United States Patent
Ito et al.

(10) Patent No.: US 6,686,591 B2
(45) Date of Patent: Feb. 3, 2004

(54) APPARATUS FOR INSPECTING MASK

(75) Inventors: Minoru Ito, Sagamihara (JP);
Norimichi Anazawa, Shinjuku-ku (JP)

(73) Assignee: Holon Co., LTD, Tokyo (JP)

( * ) Notice: Subject to any disclaimer, the term of this patent is extended or adjusted under 35 U.S.C. 154(b) by 176 days.

(21) Appl. No.: 10/048,430

(22) PCT Filed: Feb. 13, 2001

(86) PCT No.: PCT/JP01/00979
§ 371 (c)(1),
(2), (4) Date: Jan. 31, 2002

(87) PCT Pub. No.: WO02/23581
PCT Pub. Date: Mar. 21, 2002

(65) Prior Publication Data
US 2003/0151002 A1 Aug. 14, 2003

(30) Foreign Application Priority Data
Sep. 18, 2000 (JP) .................................... 2000-281685
Nov. 28, 2000 (JP) .................................... 2000-360924

(51) Int. Cl.[7] ............................................. H01J 37/256
(52) U.S. Cl. ........................................ 250/311; 250/397
(58) Field of Search .................................. 250/311, 397

(56) References Cited

U.S. PATENT DOCUMENTS 5,923,034 A  *  7/1999  Ogasawara et al. .......... 250/311

* cited by examiner

Primary Examiner—Kiet T. Nguyen
(74) Attorney, Agent, or Firm—Staas & Halsey LLP

(57) ABSTRACT

An electronic beam transmitting through a mask is detected by a detector in which a plurality of elements is aligned in a plurality of lines while an image signal is transferred by the detector synchronously with movement of the mask, and high resolution due to a short wavelength of the electronic beam can be effectively utilized as well as an image signal is transferred at right angles to a line of the detector synchronously with same time detection of pixels in a direction of the line, so that an inspection of a mask with high resolution at high speed would be achieved, and furthermore, it would be achieved to produce an image scanned in a straight line with the extremely high accuracy without zigzag scan when a stage with an easy structure is used.

13 Claims, 12 Drawing Sheets

[STEP MOVEMENT → CONTINUOUS MOVEMENT ↕ ]

FIG. 5

| Item | Present invention | Related art |
|---|---|---|
| Detecting sensitivity | 30 nm | 50 nm |
| Effective sampling rate | 200 MHz | 7.9 MHz |
| Scanning time per 1 cm² | 12 minutes | 3 hours and 30 minutes |
| Beam current density | 7 mA/cm² | 56 A/cm² |
| Beam deflection | Unnecessary | Necessary |

APPARATUS FOR INSPECTING MASK

FIELD OF THE INVENTION

The present invention relates to a technical method that an electronic beam transmitting through a mask is detected by means of a detector, in which a plurality of elements is aligned in a plurality of lines, as well as transferred synchronously with movement of the mask, so that it would be achieved to inspect a mask with high resolution at high speed. The invention also relates to a technical method that, in scanning in a straight line at right angles to a direction of the plural elements of a CCD sensor with an electronic beam illuminating the mask, an electronic beam is scanned in a straight line with the extremely high accuracy without zigzag scan when a stage with an easy structure is used.

DESCRIPTION OF THE RELATED ART

Conventionally, inspection of a mask (reticle mask) for exposing an LSI circuit pattern or such on a wafer is carried out by illuminating a mask entirely by light, measuring the strength of the light transmitting through the mask so as to obtain its image, and then, referring to a circuit diagram. In the inspection by means of light, resolution is limited by a wavelength of the light, and the current highest resolution is around 0.1 mm.

On the other hand, a scan type of electronic microscope (referred to SEM, hereinafter) is used for scanning an electronic beam narrowed down and radiated on a circuit pattern of a wafer after exposure and development with a mask so that a second electron, which is generated in the above scan, is detected to be used for inspecting a detailed structure of the above circuit pattern. A thin film forming a pattern in a stencil mask, however, has a thickness of around 2 to 20 mm, and when it is assumed that a minimum size of an opening portion of the pattern be 0.4 mm, an aspect ratio would be 5 to 50, which is extremely large compared with that of a usual structure of a surface of a wafer. Thus, the second electron generated in the opening portion cannot be taken to the outside even when the usual SEM is used to radiate an electronic beam narrowed down for scanning, and it causes a problem that the inside of the above opening cannot be inspected practically.

In the above-mentioned conventional SEM for inspecting a wafer, an electronic beam narrowed down is radiated while scan (so-called raster-scan) is performed respectively in the X and Y directions, and the second electron generated in the scan is detected so that a second electronic image would be displayed on a screen. Therefore, a time necessary to obtain whole signals (images) in a certain area on a wafer is: the number of whole pixels in a certain area X sampling time, wherein the sampling time is usually around 0.13 ms. When it is assumed that detection sensitivity be 30 nm, a time necessary to inspect 1 cm$^2$ of a sample surface is:

0.13 $ms$×1 $cm^2$/(50 $nm$)=5,200 seconds=86 minutes=1 hour and 26 minutes.

In the above calculation, a time necessary for inspection such as a time for moving a stage, for example, is entirely omitted, while it takes much more time practically. Accordingly, there is also a basic problem that such a raster-scan type of apparatus is not suitable for practical use since it needs about one and half hours to inspect 1 cm$^2$ of a sample.

In order to solve the problems, an object of the invention is to achieve inspection of a mask with high resolution at high speed by detecting an electronic beam transmitting through a mask by means of a detector, in which a plurality of elements is aligned in a plurality of lines, as well as transferring an image signal by the above detector synchronously with movement of the mask, so that high resolution due to a short wavelength of the electronic beam would be effectively utilized and that an image signal is transferred at right angles to a line of the detector synchronously with same time detection of pixels in a direction of the line.

Another object of the invention is to form an image scanned in a straight line with the extremely high accuracy without zigzag scan when a stage with an easy structure is used, by illuminating a sample (mask) by an electronic beam while scanning in a straight line at right angles to a direction of plural elements of a CCD sensor, detecting a moving and shifting amount in a direction of right angles to a direction of the scan, and correcting an electronic beam by deflection or by means of a sample moving mechanism, so that the scan of the sample (mask) can be performed in a straight line with respect to an electronic beam with extremely high accuracy.

DISCLOSURE OF THE INVENTION

In the invention, it is arranged that, as shown in FIG. 1, an electronic beam emitted from an electron gun 3 illuminates/a mask 1 through a condenser lens 4, an objective lens 5 forms an image of the electronic beam having transmitted through the mask 1, a CCD 9, which is a detector, detects an image transduced into light by a transducer 7 here, a controlling device 15 controls a stage 2 to move the mask 1 and synchronously transfers an image signal at right angles to a line of the CCD 9, and the image signal outputted from the CCD 9 is displayed or recorded.

In the above arrangement, it is repeated that the controlling device 15 controls the stage 2 to move the mask 1 at a predetermined width in a certain direction or in a direction adverse to the certain direction, so that the whole surface of the mask 1 can be scanned.

It is also arranged that the controlling device 15 would control the stage 2 to move the mask 1 continuously.

Further, it is arranged that an amount of an X ray would be reduced by disposing before a CCD, which is a detector, a board that cuts off the X ray and that an optical image passes through, or by forming on the CCD, which is a detector, by means of a lens an optical image that is transduced from an image of an electronic beam by an electronic beam-light transducer disposed obliquely.

It is also arranged that a location of the mask fixed on a sample table would be measured by means of a laser interference measuring instrument so that the mask would be moved.

Moreover, it is arranged in the invention, as shown in FIG. 10, that an electronic beam emitted and focused by an electron gun 1 and a focusing lens 3 illuminates a sample (mask) 4, a transmitted electronic beam or an electronic beam reflected (reversed) at a surface of the sample (mask) 4, to which a minus voltage not shown in the drawings is applied, is formed into an image on an objective lens 6, and a CCD sensor 14 detects the formed electronic image directly or an optical image having been transduced into light by a fluorescent screen 10. Under this condition, a stage 5 is scanned in a straight line at almost right angles to a direction of a plurality of elements of the CCD sensor 14 while a moving and shifting amount at right angles to a direction of the scan is detected, and thereby, a controlling signal is outputted to a moving mechanism of a deflector 8 or a sample 4 so as to correct the moving and shifting amount.

In the above arrangement, a plurality of pixels is disposed as the CCD sensor 14 in a straight line with respect to the formed image so as to form a detector, in which an electric charge is transferred and accumulated in a direction of right angles adjacently to the plurality of pixels disposed in a straight line synchronously with the scan of an electronic beam and in which a line or a plurality of lines of the plurality of pixels is provided in a straight line.

It is also arranged that a CCD sensor comprising a plurality of detecting elements in a straight line for detecting an electronic image directly, or a CCD sensor comprising a plurality of detecting elements in a straight line for forming and detecting an optical image having been transduced from an electronic image would be used as a detector.

Furthermore, it is arranged that a rotating device for making a direction of the scan almost same in a direction of right angles to the plurality of pixels in a straight line of the CCD sensor would be provided.

It is also arranged that an electronic beam would be formed into a shape of a band so as not to illuminate unnecessary part of the mask (sample) 4.

BRIEF DESCRIPTION OF THE DRAWINGS

FIG. 5 shows a characteristic No. 2 of the invention.

BEST MODE FOR CARRYING OUT THE INVENTION

Embodiments and operations according to the invention will be described one by one in detail with reference to FIGS. 1 to 5.

Figure 1:
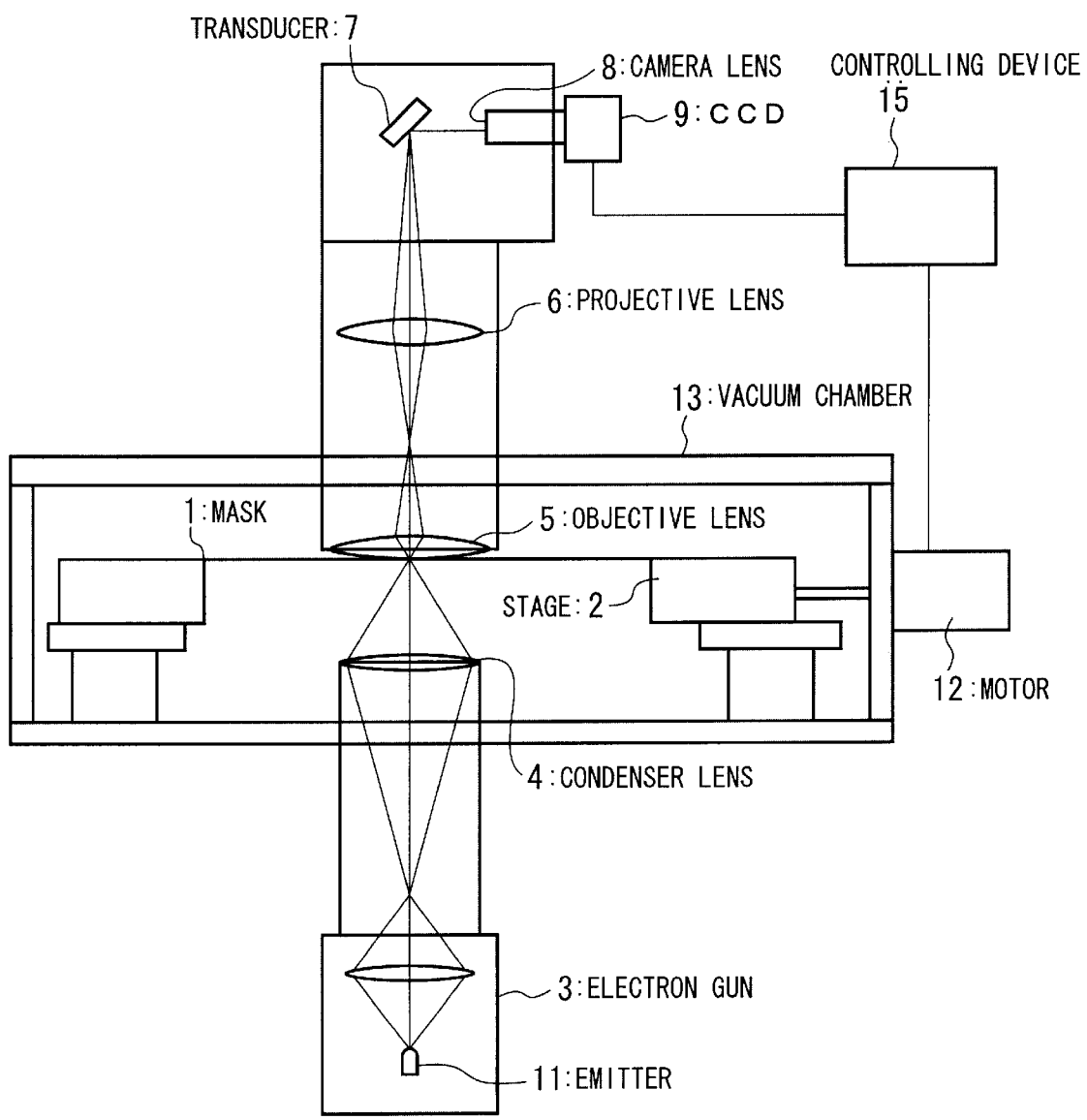
FIG. 1 is a structural diagram of a system according to the invention.

FIG. 1 illustrates a structure of a system according to the invention.

In FIG. 1, a mask 1 is provided for undergoing a transmission type of inspection.

A stage 2 is driven by a motor 12 to move the mask 1 in X and Y directions. A moving amount of the mask 1 in the X and Y directions may be measured accurately on the basis of an optical interference range instrument, which is not shown in the drawings, so that the above moving amount can be controlled.

An electron gun 3 is used for emitting an electronic beam. It accelerates at a high voltage and emits an electronic beam emitted from an emitter 11.

A condenser lens 4 focuses the electronic beam emitted from the electron gun 3 to illuminate the mask 1.

An objective lens 5 forms an image of the electronic beam transmitted through the mask 1.

A projective lens 6 magnifies and projects an image of the electronic beam formed by the objective lens 5 on a transducer 7.

The transducer 7 is, for example, a plate to which fluorescent paint is applied for transducing an image of the electronic beam into an optical image.

A camera lens 8 forms on a CCD 9 an optical image on the transducer 7.

The CCD 9 is an example of a detector, in which a plurality of lines of a plurality of pixels is provided in parallel. The CCD 9 can transfer an image (an electric charge) at right angles to the lines synchronously with movement of an image of the mask 1.

The motor 12 is provided for moving the stage 2 in the X and Y directions.

A vacuum chamber 13 is a chamber for disposing the mask and the stage 2 in a vacuum.

A controlling device 15 controls the motor 12 to control movement of the mask 1 mounted on the stage 2 in the X and Y directions, and supplies the CCD 9 with a controlling signal to control transfer of an image signal (an electric charge) at right angles to the lines synchronously with movement of an image of the mask 1 projected on the above CCD 9.

Next, an operation in the structure shown in FIG. 1 will be described.

(1) The electronic beam emitted from the electron gun 3 is focused by the condenser lens 4 to illuminate a predetermined range of the transmission type of mask 1. The electronic beam transmitted through a hole on the mask 1 is formed into an image on the transducer 7 at a predetermined magnification by the objective lens 5 and the projective lens 6 to produce an optically transduced image. The optically transduced image is formed into an image on a detection surface of the CCD 9 by the camera lens 8. The detected image signal is stored in an image memory not shown in the drawings in accordance with control by the controlling device 15.

(2) The controlling device 15 repeatedly controls the motor 12 under a condition of (1) so as to continuously move the mask 1 mounted on the stage 2 at a predetermined width in a certain direction (refer to the later-mentioned FIG. 4(*b*) for example) and continuously move the mask 1 in the adverse direction at a predetermined width next to the moved part at the end of the mask 1. At this time, an image signal (an electric charge) is synchronously transferred one by one to lines (32 lines in total, for example), which are arranged at right angles to lines comprising a plurality of optical detecting elements of the CCD 9 (line comprising 4096 elements, for example), and the above image signal (electric charge) on the CCD 9 are transferred synchronously with the images having transmitted through the mask 1. Thus, in the case that the CCD 9 comprises 32 lines, for example, 32 transfers would be performed and the strength of the image signal (electric charge) would be thirty-twofold, and thereby, it would be possible to output the image signals in parallel (to output in parallel image signals comprising 4096 pixels, for example) outside from the end of the above CCD 9. In this example, the strength of the image signal would be thirty-twofold, so that the mask 1 can be moved at the thirty-twofold speed in the case that the strength of the image signal may be equivalent to one line. It means that the moving speed of the mask 1 results in comparatively fast, as the number of lines increases, and thereby, it would be possible to scan the mask 1 entirely at a predetermined width at an extremely high speed (however, the mask 1 can be moved when the transfer of the image signal (electric charge) from one line of the CCD 9 to another line is sufficiently fast, while the movement is limited by the speed of transfer of the electric charge when the transfer is not so fast).

As described above, it is repeated that an electronic beam is radiated in a plane shape from one surface of the transmission type of mask 1, an image of the transmitted electronic beam is transduced into an optical image by the transducer 7, the transduced optical image is formed into an image on elements of the CCD 9, and the image signal of pixels of a line comprising a plurality of elements of the above CCD 9 is transferred at right angles with the lines synchronously with movement of the mask 1. Thus, it would be possible to increase the speed of scanning the mask 1 at a predetermined width relative to the number of lines of the CCD 9, for example, so that the speed can be thirty-two times or two hundreds and fifty-six times as fast with an extremely easy structure when the number of lines of the CCD 9 is 32 or 256, for example. It will be described in detail hereinafter.

Figure 2:
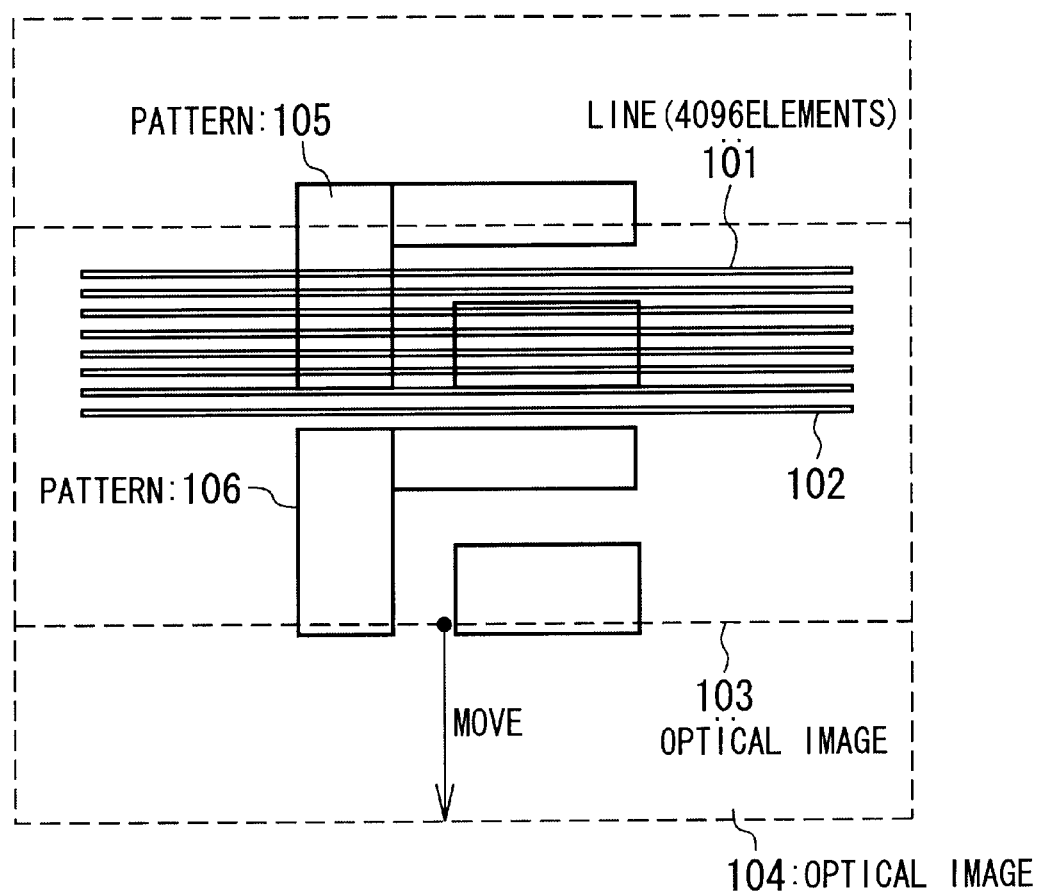
FIG. 2 shows an example of a detector according to the invention.

FIG. 2 shows an example of a detector according to the invention. It is a simplified diagram of a part of the structure of the CCD 9 shown in FIG. 1 and shows an example of an arrangement of a detection surface (detecting element) of the CCD 9 and an optical image projected on the above detection surface. A plurality of lines 101 of the CCD 9, eight lines in FIG. 2, is aligned. One line comprises 4096 elements of the CCD 9. A pattern 105 is an example of a projected pattern of the optical image of the electronic beam having transmitted the mask 1. In this case, when it is assumed that total magnification of the objective lens 5, the projective lens 6 and the camera lens 8 shown in FIG. 1 be 430 times and a size of one pixel of the CCD 9 be 13 mm square, one pixel on a surface of the mask 1 equals to 0.03 mm square. When it is assumed that a line of the CCD 9 would comprise 4096 pixels, the line would be about 53 mm on the CCD 9 and 123.8 mm on the mask 1.

Here, when the stage 2 to which the mask 1 is mounted is moved, the optical image is moved from a location 103 to a location 104 at right angles to a direction of the line on a surface of the CCD 9 in response to the movement of the stage 2. Transfer of an electric charge to each line of the CCD 9, which is synchronous with the speed of movement of the optical image, enables synchronous accumulation for the number of lines, that is, eight fold synchronous accumulation in the case of eight lines as shown in FIG. 2, for example. Accordingly, in the case of an image signal with a same electric charge in a line, the optical image can be moved (the mask 1 can be moved) at the eight fold speed, so that high-speed scanning can be achieved. In this synchronous control, the controlling device 15 shown in FIG. 1 controls to drive the motor 12 to continuously move the stage 2 to which the mask 1 is mounted, and then, transfer of an electric charge in a direction of a line of the CCD 9 would be controlled synchronously. The image signal outputted from the CCD 9 is stored in an image memory not shown in drawings or displayed on a screen by the controlling device 15. A transmitted image of the mask 1 accumulated in the image memory is referred to design data of the above mask 1 so that it can be possible to inspect defects of the mask 1 (defects such as a redundant pattern and missing of a pattern).

In this embodiment, there are two kinds of transmission type of mask 1: a mask with a supporting film and a mask without a supporting film. The mask 1 without a supporting film has a gap at an opening portion, and thus, the electronic beam at a low acceleration voltage is made to illuminate the above mask 1 so as to transmit the opening portion in order to achieve an image. On the other hand, the mask 1 with a supporting film usually has at the opening portion the supporting film that is as thick as about 0.1 mm. Thus, the electronic beam at a low acceleration voltage is selected properly (10 KV to 50 KV, for example) so that S/N preferable as an image of the electronic beam having been transmitted through the above supporting film portion can be achieved.

Figure 3:
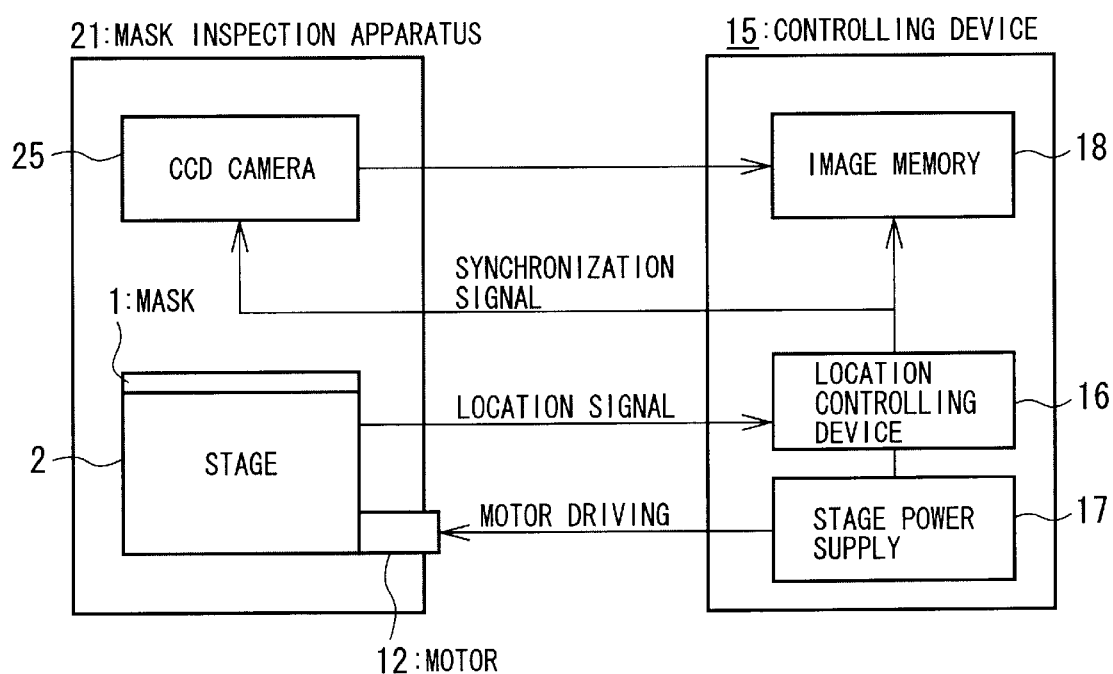
FIG. 3 illustrates a structural diagram of a system of an integral part according to the invention.

FIG. 3 is a structural diagram of a system of an integral part according to the invention. FIG. 3 shows an example of a system structure for describing synchronous control between movement of the mask 1 in a mask inspection apparatus 21 and movement (transfer) of an image (electric charge) to a direction of right angles to a line on the CCD.

In FIG. 3, the mask inspection apparatus 21 has an almost same structure as that of FIG. 1 and comprises a stage 2, to which a mask 1 is attached, and a CCD camera 25.

The CCD camera 25 comprises the transducer 7, the camera lens 8 and the CCD 9 shown in FIG. 1. It transduces an image of an electronic beam into an optical image to form an image on the CCD 9, and transfers the electric charge at right angles to the line synchronously with the movement of the optical image by means of the CCD 9, which comprises a plurality of lines as shown in FIG. 2 and as described above, so as to enable a high-speed detection.

A controlling device 15 corresponds to the controlling device 15 shown in FIG. 1 and comprises a location controlling device 16, a stage power supply 17 and an image memory 18 in FIG. 3.

The location controlling device 16 controls a location of movement of the transmission type of mask 1 attached to the stage 2. The location controlling device 16 controls and drives the motor 12 to control movement of the stage 2 (the mask 1) on the basis of a location signal from the stage 2 shown in the drawings or a location signal of a location of the stage 2 (the mask 1) accurately measured by means of a laser interference measuring instrument not shown in the drawings.

The stage power supply 17 supplies a motor 12 with power for driving the motor on the basis of a signal from the location controlling device 16 so as to move the stage 2.

The image memory 18 accumulates images corresponding to the electronic beam, which has been outputted from the CCD camera 25 and which has transmitted through the mask 1.

Next, an operation will be described.

The location controlling device 16 supplies the motor 12 with power via the stage power supply 17 on the basis of a location signal from the stage 2, and continuously moves the mask 1 attached to the stage 2 from a predetermined location at a predetermined width at a certain speed in a certain direction, as shown in FIG. 4(*b*) mentioned later, for example. A synchronization signal is supplied to the CCD camera 25 synchronously with this control of movement of the mask 1, and an electric charge of the image is transferred so as to correspond to movement of the image to a direction of right angles to lines of the CCD 9 of the above CCD camera 25 after transmitted through the mask 1, as described in FIG. 2 mentioned above. Synchronous control of the location controlling device 16 synchronizes movement of the image of the electronic beam having transmitted through the mask 1 with transfer (movement) of the electric charge of the image at right angles to a line of the CCD 9 of the CCD camera 25. For example, when the number of lines is 32, an image signal amplified thirty-two times as much is outputted in parallel from a line at the last end of the CCD 9, so that the image signal outputted in parallel would be accumulated in the image memory 18 as well as displayed on a displaying apparatus not shown in the drawings. Further, it becomes possible that a pattern of the image of the electronic beam having transmitted through the mask 1, which is accumulated in the image memory 18, is referred to a pattern on the basis of design data so that existence of defects would be automatically inspected. At this time, the location controlling device 16 controls movement of the mask 1 and transfer of the electric charge at right angles to a line of the CCD 9 synchronously. Thus, the strength of the image having transmitted through the mask 1 for the times as much as the number of lines can be obtained, which enables a high-speed scanning for the times as fast as the number of lines.

FIG. 4 shows diagrams illustrating a characteristic No. 1 of the invention.

Figure 4A:
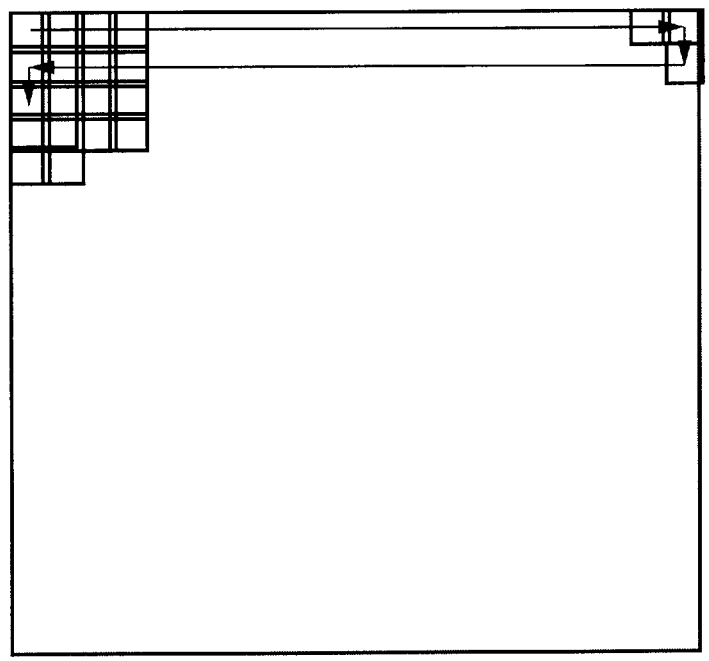
FIGS. 4(*a*) and 4(*b*) illustrates a characteristic No. 1 of the invention.

FIG. 4(a) shows an example of a conventional method (a step and repeat method). In the step and repeat method, an image is accumulated for a predetermined time period in a stationary state after waiting until a step movement of every one pixel (or every rectangular range of a plurality of pixels) stops, and is stored in an image memory to repeat next step movement similarly so that the entire mask 1 is painted out by rectangular ranges as shown in FIG. 4(a) to accumulate the whole image in the image memory. Thus, it is necessary to wail until the vibration stops after the step movement. Further, it is repeated that an electric charge is accumulated in the CCD for an sufficient time period to obtain an enough S/N under a stationary state (an electric charge is accumulated for a time period about thirty-two times as much as the case that the number of lines described in FIG. 2 showing an embodiment according to the invention is thirty-two, for example, in order to obtain a same S/N ratio), and then, the electric charge accumulated in the CCD is outputted and accumulated in the image memory, so that one step is completed and the next step is started. This causes a problem that pretty much time is required to obtain an entire image of the mask 1.

Figure 4B:
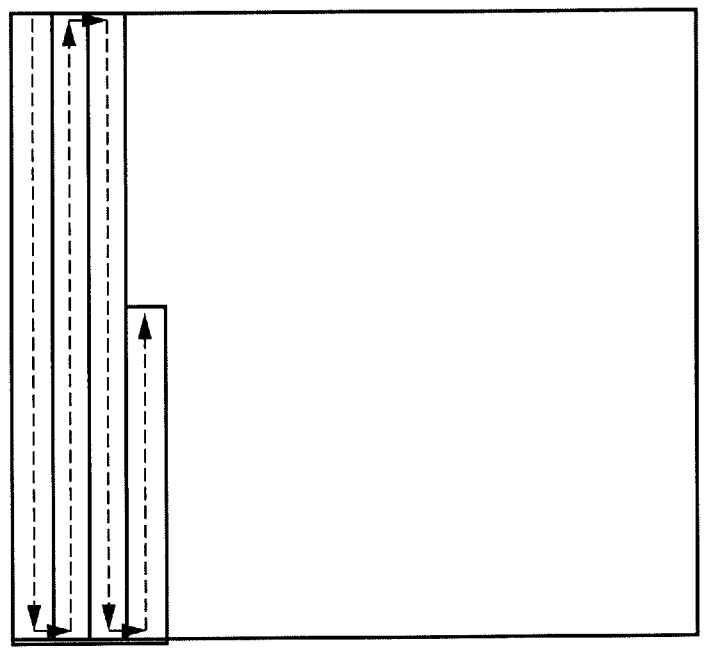

FIG. 4(b) shows an example according to the invention (continuous movement). In a continuous movement method according to the invention, it is repeated that the mask 1 is continuously moved at a width corresponding to a line comprising a plurality of pixels (a line comprising 4096 pixels, for example) as shown as a dotted arrow in FIG. 4(b) in a certain direction while an electric charge is transferred synchronously at right angles to a line of the CCD 9, an image signal continuously outputted from the end of a line of the above CCD 9 is accumulated in the image memory until the movement is continued to the end of the mask 1, and the mask 1 for the next width is moved continuously in an adverse direction from the end of the mask 1 (or after passing over a little bit the end of the mask 1), and then, the entire mask 1 is painted out so that the whole image is accumulated in the image memory. Thus, it is enough that the mask 1 is continuously moved at a predetermined width to be painted out so that an image signal outputted from the CCD 9 at that time would be accumulated continuously in the image memory. Accordingly, the whole image of the mask 1 can be obtained at an extremely high speed.

FIG. 5 shows a characteristic (No. 2) according to the invention. FIG. 5 shows an example of comparison between the continuous movement method according to the invention shown in FIG. 4(b) and the conventional method that an electronic beam narrowed down is raster-scanned. Items for comparing the both methods are as follows:

Detection sensitivity: the detection sensitivity is an example of the minimum resolution on the mask 1;

Effective sapling rate: this is a sampling rate, which is effective. The sampling rate in the invention is high since one line comprises 4096 pixels. It is slow in the conventional method since the electronic beam scans every pixel;

Scanning time per 1 cm$^2$: one line described above comprises a plurality of pixels in the invention, and the electric charge is transferred synchronously with movement of the mask 1 between plural lines. Thus, high-speed scan becomes possible;

Beam current density: this is the density of an electronic beam illuminating the mask 1; and Beam deflection: this is whether the electronic beam illuminating the mask 1 is deflected or not. The deflection of the electronic beam is not necessary in the invention since the mask 1 is continuously moved.

As described above, it is possible to obtain an image by scanning at speed of 12 minutes per 1 cm$^2$ in the invention, while it takes no less than three and a half hours in the conventional method (a method of raster-scan of an electronic beam). Accordingly, it is possible in the invention to scan a wide range of the mask 1 at an extremely high speed to obtain an image with high resolution.

Figure 6:
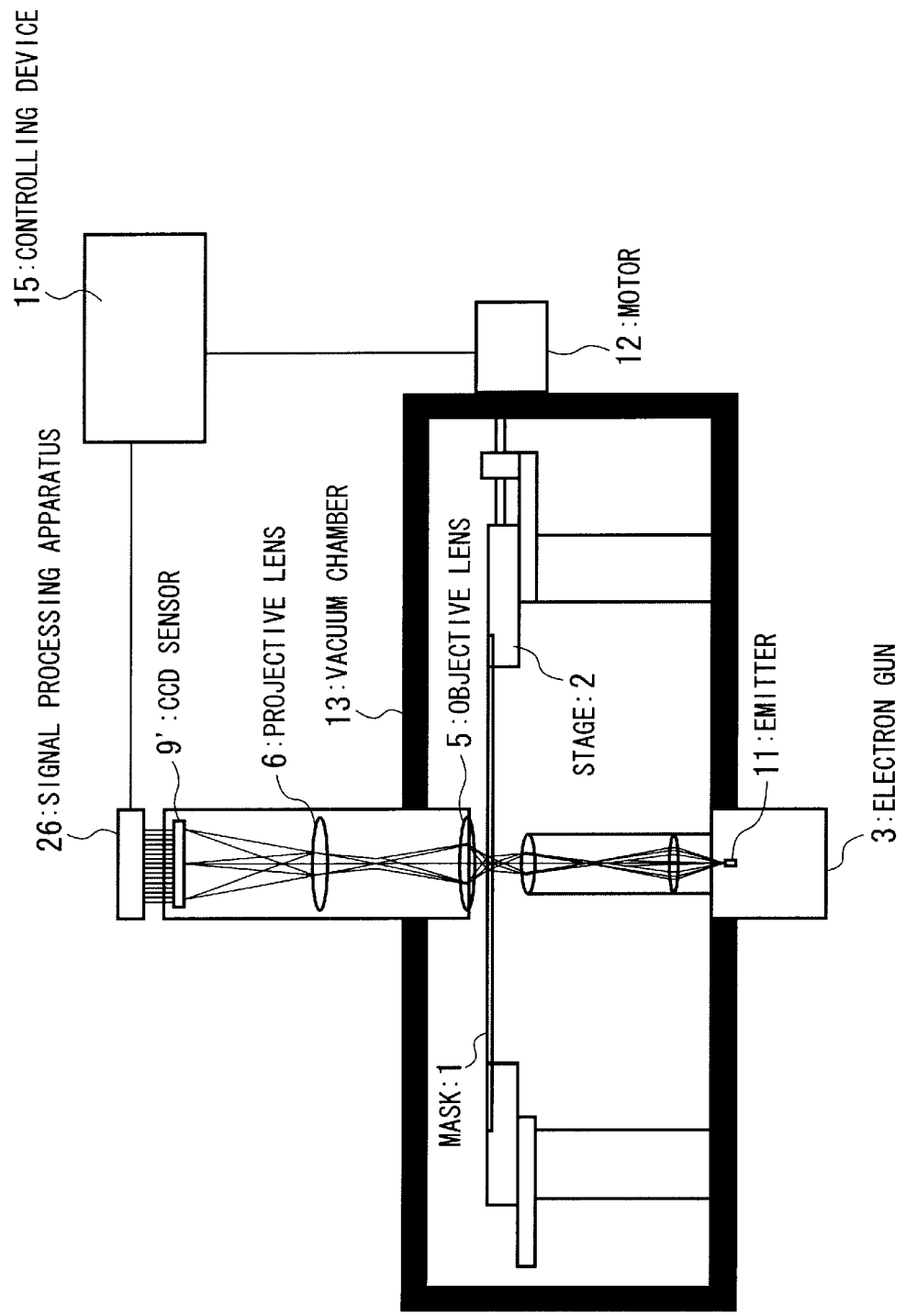
FIG. 6 is a structural diagram of another embodiment No. 1 according to the invention.

FIG. 6 shows a structural diagram of another embodiment No. 1 according to the invention. In FIG. 6, a mask 1, a stage 2, an electron gun 3, an emitter 11, an objective lens 5, a projective lens 6, a motor 12, a vacuum chamber 13 and a controlling device 15 are same as those having the same reference numbers in FIG. 1 mentioned above, and therefore, their description is omitted here.

In FIG. 6, a CCD sensor 9' detects directly an image of an electronic beam, which has been formed into an image by the projective lens 6.

A signal processing device 26 transfers an image signal (an electric charge) of the CCD sensor 9' synchronously with movement of the stage 2 (movement of the mask 1) as mentioned above so as to output a reinforced (amplified) image signal.

As described above, an image of the electronic beam having transmitted through the mask 1 is directly formed on the CCD sensor 9' to be amplified by moving the mask 1 synchronously with movement of an electric charge or by moving the electric charge synchronously with movement of the mask 1, so that it would be possible to detect an image signal with a preferable S/N ratio.

Figure 7:
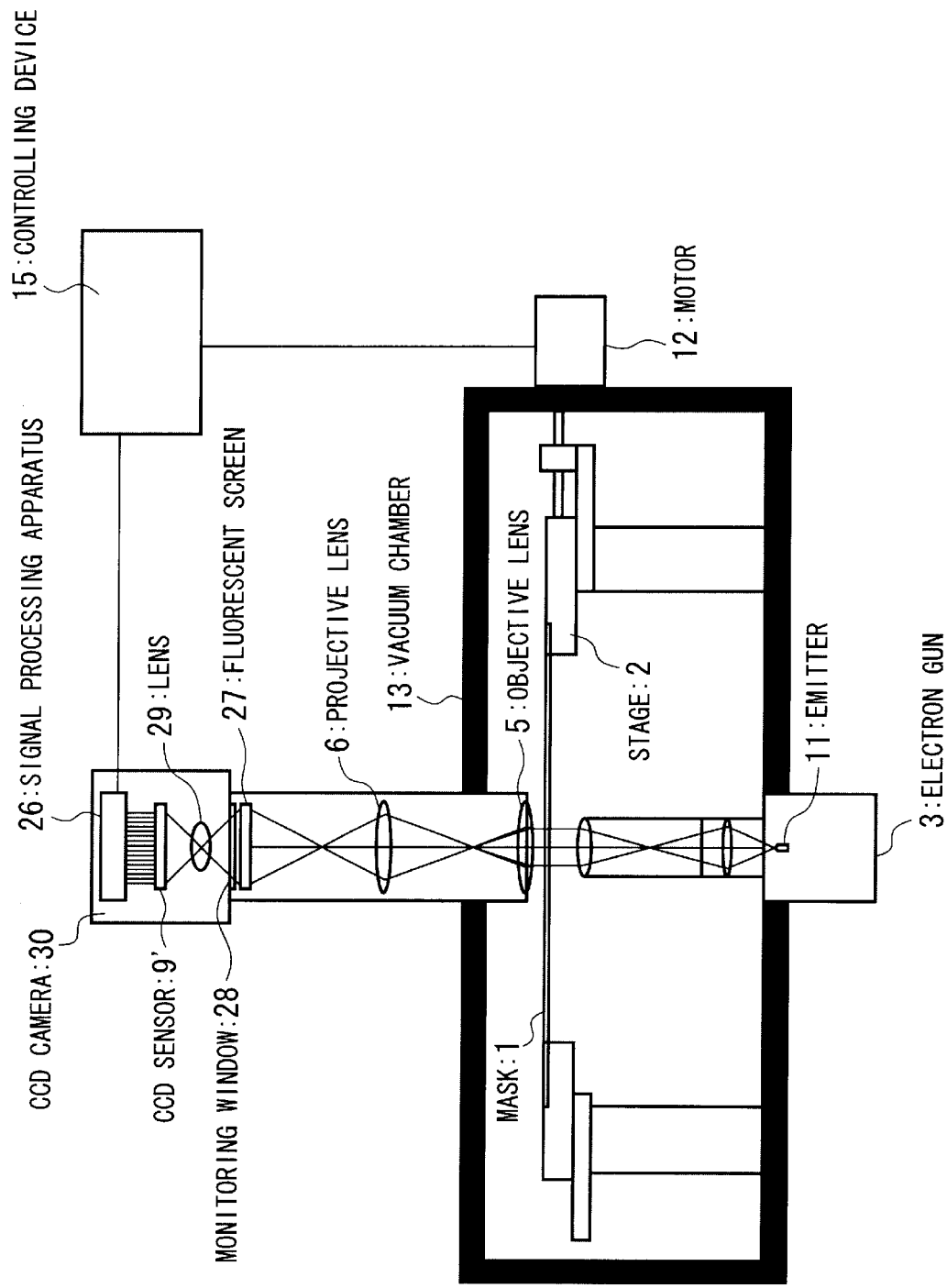
FIG. 7 is a structural diagram of another embodiment No. 2 according to the invention.

FIG. 7 shows a structural diagram of another embodiment No. 2 according to the invention. In FIG. 7, a mask 1, a stage 2, an electron gun 3, an emitter 11, an objective lens 5, a projective lens 6, a motor 12, a vacuum chamber 13 and a controlling device 15 are same as those having the same reference numbers in FIG. 1 mentioned above, and therefore, their description is omitted here.

In FIG. 7, a fluorescent screen 27 is a transparent board (glass, for example) on which a thin fluorescent material is applied, and is projected from the lower part of the drawing an image of the electronic beam to be transduced into light so that the optical image would be emitted upward.

A monitoring window 28 is a transparent board (glass, for example) for maintaining a vacuum condition. The fluorescent screen 27 and the monitoring window 28 may be formed into one body. In this case, an X ray or such is generated in forming the image of the electronic beam on the fluorescent screen 27. Therefore, the generated X ray or such is cut off or reduced by means of a board of the fluorescent screen 27 or a board of the monitoring window 28 (for example, lead glass for cutting off/reducing the X ray or a board for cutting off/reducing a wavelength that is desired to be cut off) so that the decrease of the S/N ratio of the CCD sensor 9' can be prevented.

A CCD camera 30 detects and amplifies an optical image emitted from the monitoring window 28. In FIG. 7, the CCD camera 30 comprises a lens 29, a CCD sensor 9' and a signal processing device 26 shown in the drawings.

The lens 29 forms on the CCD sensor 9' an optical image transduced and emitted by the fluorescent screen 27.

The CCD sensor 9' detects an optical image formed by the lens 29.

The signal processing device 26 transfers an image signal (an electric charge) of the CCD sensor 9' synchronously with movement of the stage 2 (movement of the mask 1) as described above so as to output a reinforced (amplified) image signal.

As described above, an image of the electronic beam having transmitted through the mask 1 is transduced into an optical image by a transmission type of the fluorescent screen 27 and the transduced optical image is formed on the CCD sensor 9' by the lens 29 so as to be amplified by moving the mask 1 synchronously with movement of an electric charge or by moving the electric charge synchronously with movement of the mask 1, so that it would be possible to detect an image signal with a preferable S/N ratio.

Figure 8:
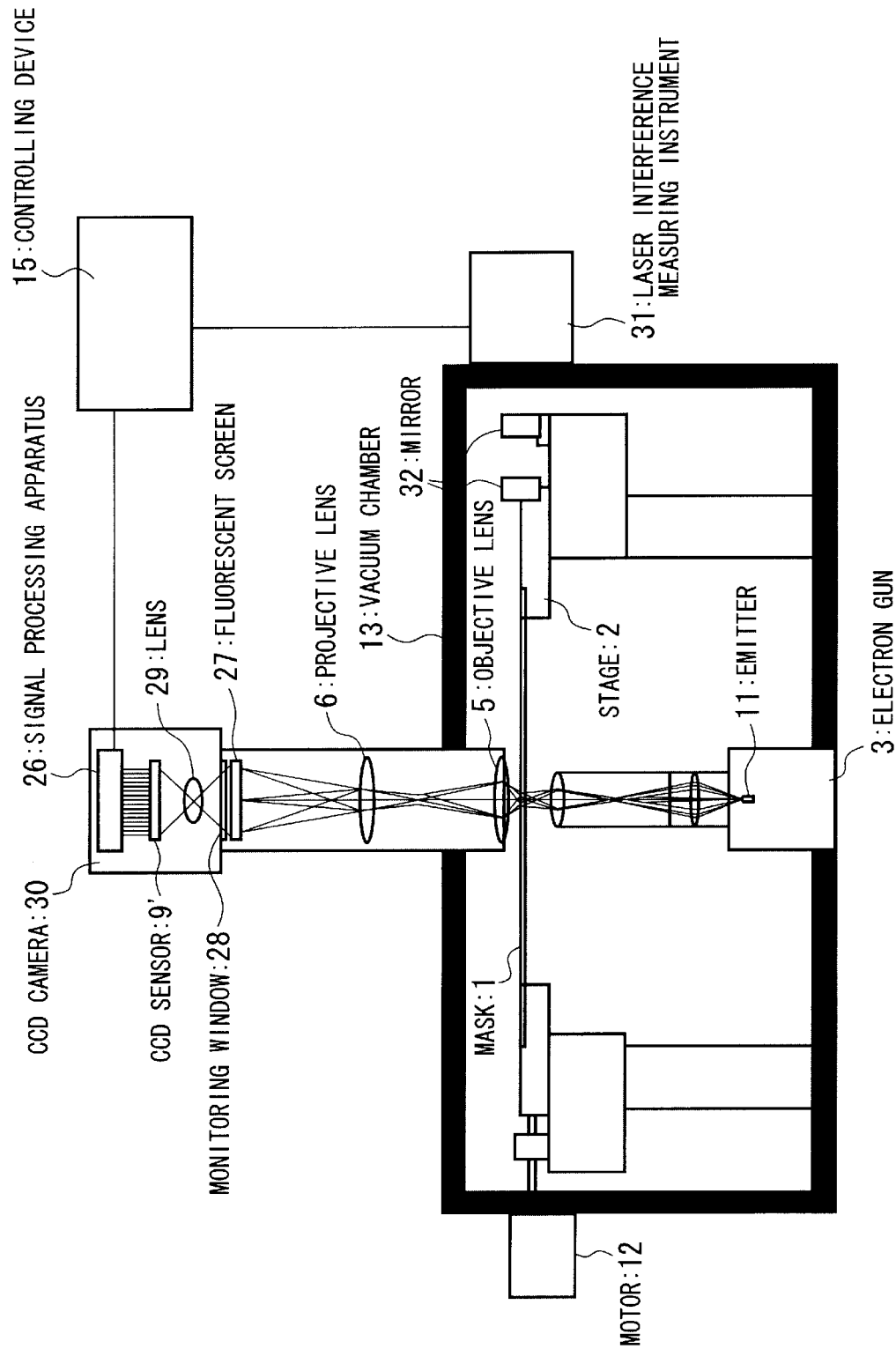
FIG. 8 is a structural diagram of another embodiment No. 3 according to the invention.

FIG. 8 shows a structural diagram of another embodiment (No. 3) according to the invention. In FIG. 8, in addition to the embodiment shown in FIG. 7, a so-called laser interference measuring instrument 31 for measuring a distance by using interference of a laser beam between a mirror 32 fixed to the stage 2 and a mirror 33 fixed on a fixing table 34 is further used to detect movement of the stage 2 (movement of the mask 1) with high accuracy (to detect a moving amount in the X direction with high accuracy), and what is similar to the instrument is also provided in a direction of right angles to detect a moving amount in the Y direction with high accuracy. On the basis of these amounts of detection, an image is amplified synchronously with movement of an electric charge of the image on the CCD sensor 9', so that it would be possible to make the S/N ratio high and to output a fine image.

As described above, it would be possible to measure a real-time amount of movement of the stage 2 with high accuracy by means of the laser interference measuring instrument, to amplify an image by synchronizing the measured moving amount with transfer of an electric charge of the CCD sensor 9' and to produce a transmission image of the mask 1 at a high S/N ratio.

FIG. 9 is a structural diagram of another embodiment No. 4 according to the invention. In FIG. 9, an example of the transducer shown in FIG. 1 is shown.

Figure 9A:
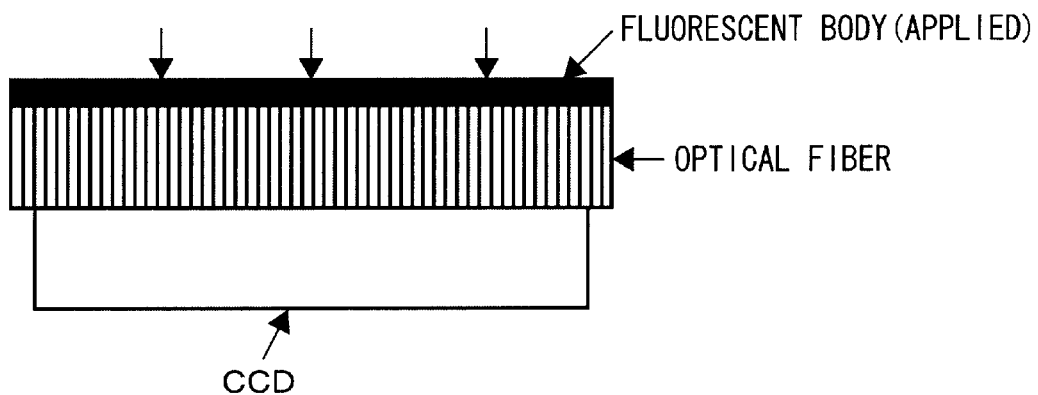
FIGS. 9(*a*) and 9(*b*) are a structural diagram of another embodiment No. 4 according to the invention.

FIG. 9(a) shows an example of a transducer that a CCD, an optical fiber and a fluorescent body are formed into one body. In FIG. 9(a), both ends of an optical fiber are respectively flatted and polished so that the fluorescent body would be applied to one end and the CCD is attached to the other end. Accordingly, when an image of an electronic beam formed in the structure shown in FIG. 1 is projected on one optical fiber, to which the fluorescent body is applied, an optical image identical to the image of an electronic beam is outputted from the other side. Then, the outputted image can be detected directly by each element of the CCD, or an image magnified or reduced, if necessary, by means of an optical lens not shown in the drawings can be detected by the CCD.

Figure 9B:
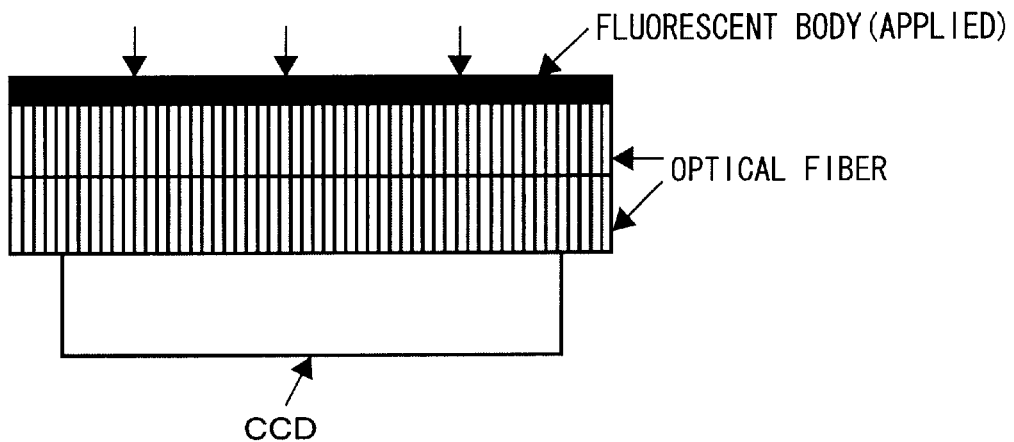

FIG. 9(b) shows an example in which the optical fiber shown in FIG. 9(a) is divided and polished to enable to connect and separate the divided portions. In this case, making a part of the optical fiber on the CCD side long can lead a signal of an optical image to any location away from a part of the optical fiber, to which the fluorescent body is applied and which is disposed in a vacuum, without weakening the signal.

Next, an operation of other embodiments according to the invention will be described in detail one by one with reference to FIGS. 10 to 12.

Figure 10:
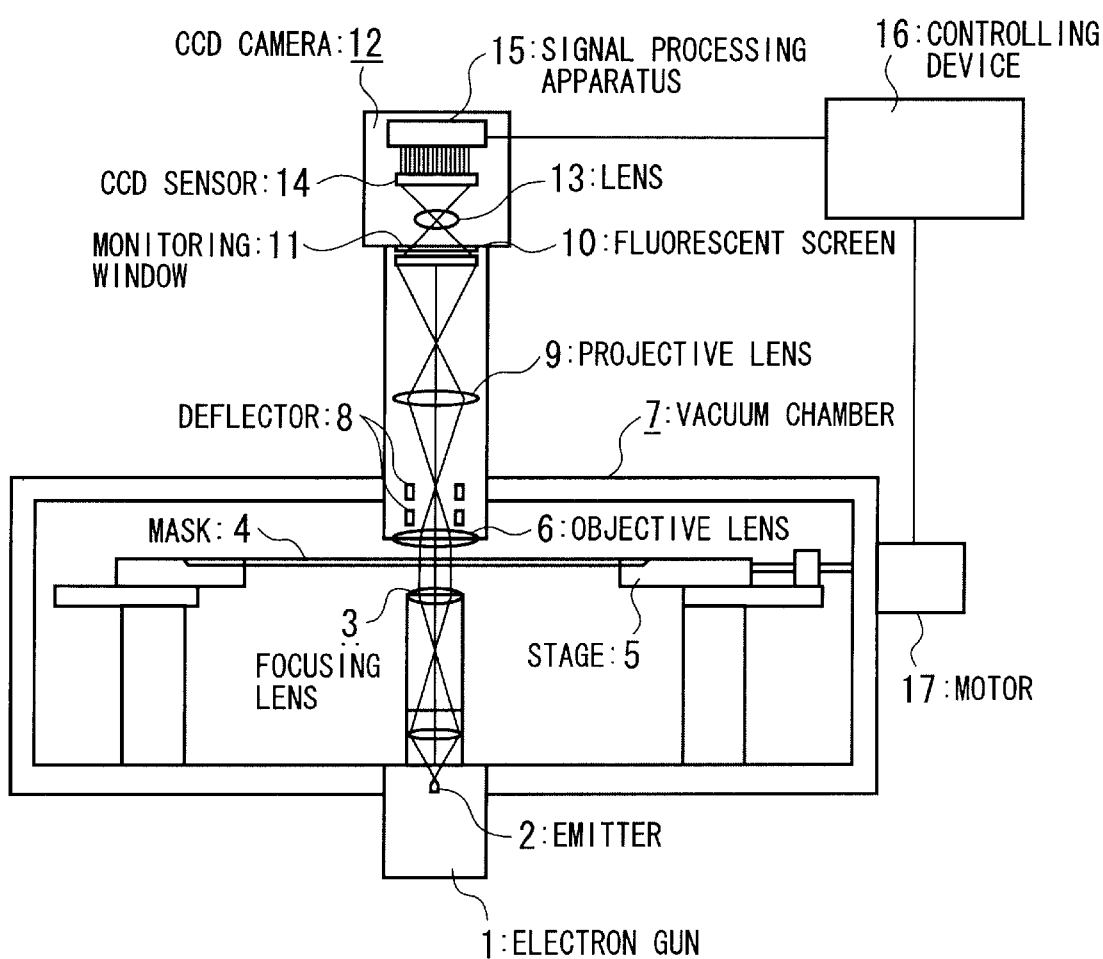
FIG. 10 is a structural diagram of a system according to the invention.

FIG. 10 is a structural diagram of a system according to the invention.

In FIG. 10, an electron gun 1 accelerates and emits an electronic beam emitted from an emitter 2. There are methods for forming an electronic beam in a shape of a band such that:

a portion at the top end of the emitter 2 for emitting an electronic beam is formed into a shape of a band so as to emit an electronic beam in a shape of a band;

a material, which is easy to emit an electronic beam, is formed into a shape of a band and attached to the top end portion of the emitter 2 so as to emit an electronic beam in a shape of a band;

a beam focus plane is formed by means of a focusing lens 3 and an electronic beam is cut out by means of a molded diaphragm so that an electronic beam in a shape of a band would be formed from a round electronic beam emitted from the electron gun 1; and a round electronic beam is formed into a shape of a band (a shape of an ellipse) by means of a four-polar lens or a multi-polar lens.

Anyway, it is all right as far as an electronic beam would be formed into a shape of a band when it transmits through a mask (sample) 4 or reflects at a vicinity of a surface of the mask (sample) 4 to which a minus voltage is applied and which is not shown in the drawings. The way of forming an electronic beam into a shape of a band is not limited to the above method.

Here, an outer shape of an electronic beam is not important in a view of the principle of the invention since a shape of the actually detected beam is determined in accordance with a shape of a detector (a CCD sensor 14). A main purpose of forming an electronic beam into a shape of a band is to prevent occurrence of heat due to vain illumination of an electronic beam on the sample (mask) 4 or to prevent pollution of a periphery by an electronic beam.

The focusing lens 3 focuses the electronic beam emitted from the emitter 2 comprising the electron gun 1.

The mask (sample) 4 is a sample (mask), which is an object in forming a magnified electronic image. In a condition shown in FIG. 10, the sample is a transmission type of mask (sample) 4. In addition, there is a reflection type of sample 4 not shown in the drawings. In the case of the reflection type of sample 4, a minus voltage is applied to the sample 4, so that an electronic beam in a shape of a band is emitted from upper or obliquely upper side in FIG. 10 to be reflected (reversed) in the vicinity of the surface and to return to the upper side due to the minus voltage applied to the above sample 4, and then, an electronic image corresponding to convex and concave shapes of the surface of the sample 4 is formed by an objective lens 6.

The stage 5, on which the mask (sample) 4 is mounted, moves the mask (sample) 4 in the X and Y directions. In this movement, moving amounts in the X and Y directions are measured accurately by means of a laser measuring instrument 23, as shown in FIG. 2 described later.

The objective lens 6 forms an image of an electronic beam in a shape of a band, which transmits through or is reflected at the mask 4, to form an electronic image. In the case of forming the reflected electronic beam in a shape of a band into an image, an electronic beam having passed through a slit located in the vicinity of a rear focus surface of the objective lens 6 not shown in the drawings contributes in forming an electronic image in a shape of a band, while an electronic beam cut off does not contribute in forming an electronic image in a shape of a band. As a result, an electronic image in a shape of a band, which has a contrast corresponding to convexes and concaves of the surface of the sample 4, is formed.

A vacuum chamber 7 is a vacuum chamber for disposing the mask 4 and the stage 5 in a vacuum so that an electronic beam is prevented from being scattered or attenuated by the air.

A deflector 8 deflects (compensates) a location of an electronic image to any direction.

A projecting lens 9 projects an electronic image formed by the objective lens 6 on a fluorescent screen 10 at an optional magnification.

The fluorescent screen 10 transduces an electronic image into an optical image.

A monitor window 11 is provided in the fluorescent screen 10 so that an optical image formed on the above fluorescent screen 10 would be taken out to the outside of a vacuum to be projected on the CCD sensor 14 in FIG. 10.

A CCD camera 12 detects an optical image formed on the fluorescent screen 10 by means of CCD elements, and comprises a lens 13, a CCD sensor 14 and a signal processing device 15. The CCD camera 12 is provided with a mechanism for rotating the CCD camera with respect to the fluorescent screen 10 and optionally adjusts a rotation angle so that an image moves (is scanned) at almost right angles to a direction of a straight line of the plural elements of the CCD sensor 14.

The lens 13 focuses (forms) an optical image formed on the fluorescent screen 10 on the CCD sensor 14.

The CCD sensor 14 is a so-called accumulation type of line sensor for providing a plurality of detecting elements in a shape of a line and in parallel at right angles so as to transfer an electric charge.

A signal processing device 15 controls the CCD sensor 14 to process a signal taken out and to output it outside.

A controlling device 16 is a controlling device for transferring a signal accumulated in the CCD sensor 14 into elements located in another adjacent line synchronously with movement of the stage 5 by means of motor 17 so as to perform an accumulation type of detection.

The motor 17 controls movement of the stage 5.

Now, an operation of a structure shown in FIG. 10 will be described.

(1) The focusing lens 3 focuses an electronic beam emitted from the emitter 2 comprising the electron gun 1 so that the emitted electronic beam would illuminate the mask (sample) 4 to generate an electronic beam having transmitted through the mask (sample) 4. In the case of a reflection type, which is not shown in the drawings, the focusing lens 3 focuses an electronic beam emitted from the emitter 2 comprising the electron gun 1 from upper or obliquely upper side so that the emitted electronic beam would illuminate the mask (sample) 4, to which a minus voltage is applied, and would reflect in the vicinity of the surface of the above mask (sample) 4 to return to the original direction.

(2) The electronic beam, which has transmitted through the mask (sample) 4 or which has reflected in the vicinity of the surface of the above mask (sample) 4 in (1), is formed into an image by the objective lens 6. Then, the image is magnified at any magnification by the projecting lens 8 to be projected on the fluorescent screen 10 here.

(3) The electronic image projected on the fluorescent screen 10 in (2) is transduced into an optical image and formed into an image on the CCD sensor 14 by the lens 13 so that an image signal having been transduced into an electric signal would be outputted. At this time, in the CCD sensor 14, plural elements are arranged in a line. The plural elements arranged in a line cut off an optical image, and as a result, only an image on the mask (sample) 4 corresponding to a part in a line, which is cut off, (a part in a shape of a band) is extracted and magnified to be detected.

(4) The stage 5 is continuously moved in a straight line at right angles to the part in a line (a part in a shape of a band), which is detected by the plural elements of the CCD sensor 14 arranged in a line in (3) and which corresponds to the mask (sample) 4, while an electric charge of a signal detected in a line of the plural elements of the CCD sensor 14 arranged in a line is transferred to a next line, which is adjacent to the above line of the plural elements of the CCD sensor 14, of the plural elements arranged in a line synchronously with the above movement. A delay-integration type of amplification is performed by repeating the above.

(5) When the mask (sample) 4 is continuously scanned in a straight line at right angles to a direction that the plural elements of the CCD sensor 14 are arranged in a line in (4), a moving and shifting amount in a direction, of right angles to a direction of the above continuous scan in a straight line is measured accurately by means of a laser measuring instrument. The mask (sample) 4 is corrected to move on the basis of the measured moving and shifting amount, or a signal is outputted to the deflector 8 so that the mask (sample) 4 is corrected to move. Accordingly, it becomes possible to achieve accurate scan in a straight line without a zigzag and at right angles to a direction that the plural elements of the CCD sensor 14 are arranged in a line.

As described above, an electronic beam illuminates the mask (sample) 4 to form an image of the electronic beam having transmitted through or reflected on the mask (sample) 4, and the formed electronic image (or an optical image further transduced into light) is projected to the CCD sensor 14 so that only a part in a shape of a straight line is detected at the part that plural elements of the above CCD sensor 14 are arranged in a straight line, while the mask (sample) 4 is scanned in a straight line at almost right angles to a direction of the straight line in which the plural elements are arranged, as well as a moving and shifting amount at right angles to a direction of the scan is measured accurately by means of a laser measuring instrument, so that movement of the mask (sample) 4 would be corrected or a signal would be outputted to the deflector 8 to correct the mask (sample) 4. Thus, the mask (sample) 4 can be moved in a straight line in a direction of scanning with the extremely high accuracy with respect to the electronic beam, so that it would be possible to form an image scanned in a straight line with the extremely high accuracy without a zigzag by means of a stage having an easy structure.

Figure 11:
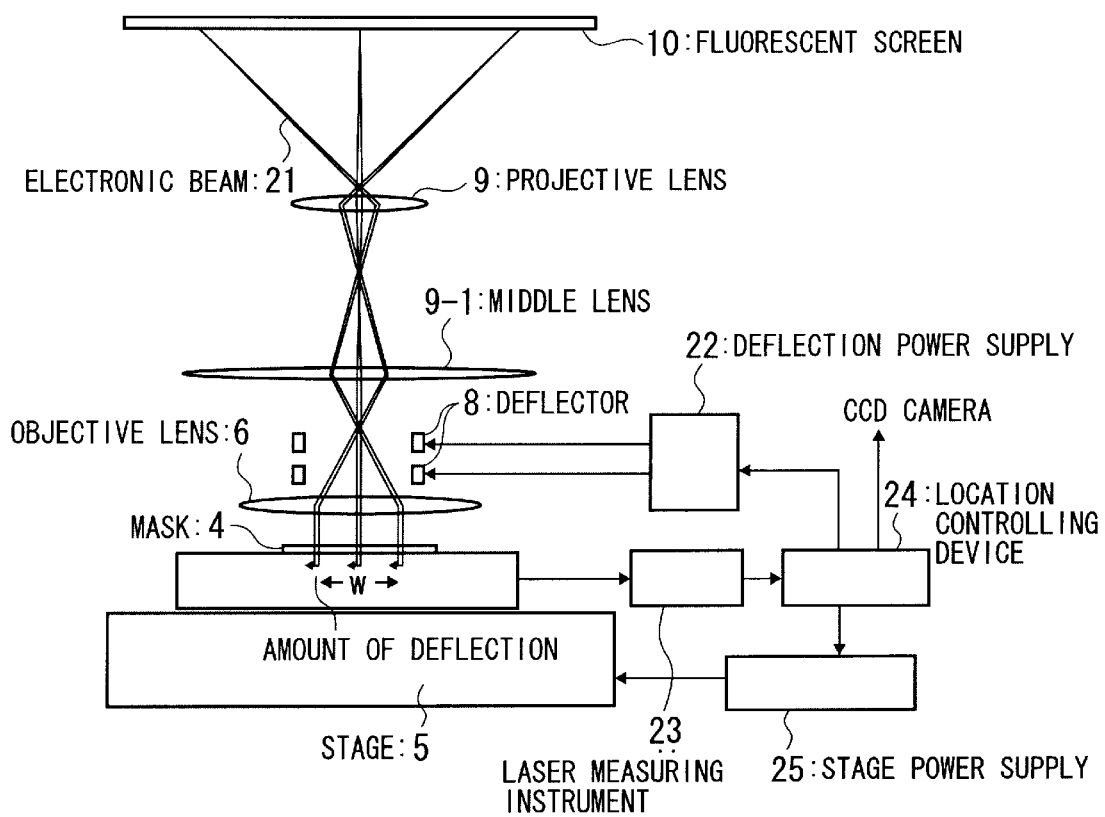
FIG. 11 is a structural diagram of an embodiment according to the invention.

FIG. 11 is a structural diagram of an embodiment according to the invention.

In FIG. 11, a middle lens 9-1 comprises a two-steps lens together with a projective lens 9 and projects an electronic image formed by an objective lens 6 at any magnification on a fluorescent screen 10.

A deflection power supply 22 is for supplying a deflector 8 with the deflection voltage or deflection current to correct the moving and shifting amount in a direction of right angles to a direction of the aforementioned scan.

A laser measuring instrument 23 is for measuring accurately respective moving amounts of the stage 5 in the X and Y directions (there are two laser measuring instruments provided for the X direction and the Y direction although they are not shown in the drawings).

A location controlling device 24 supplies the deflector 8 with an electric voltage or an electric current through the deflection power supply 22 on the basis of a moving and shifting amount of a mask (sample) 4, which is measured by means of the laser measuring instrument 23, at right angles to a direction of the scan, and corrects the above moving and shifting amount so as to control the scan to be in a straight line extremely accurately.

A stage power supply 25 is for supplying a motor for moving the stage 5 in the X and Y directions with power.

Next, an operation shown in FIG. 11 will be described.

(1) The laser measuring instrument 23 measures a moving amount of the stage 5, and the location controlling device 24 obtains a moving direction Y corresponding to a direction of a line of the CCD sensor 14 and a moving direction X corresponding to a direction of right angles to the direction of the line.

(2) It is repeated that an electric charge (a signal), which is detected in a line of plural elements of the CCD sensor 14 of a CCD camera 12 that are arranged in a straight line and which is accumulated in each element, is transferred one by one to adjacent plural elements in a straight line on the basis of a moving amount in the X direction obtained in (1).

(3) The deflector 8 is supplied with an electric voltage or an electric current so that a line of the scan is corrected for an amount corresponding to a moving and shifting amount from a straight line on the basis of the moving amount in the Y direction obtained in (1). Accordingly, an electronic image can be accurately scanned in a straight line without a zigzag at almost right angles to a direction of plural elements of the CCD sensor 14, which are arranged in a straight line.

As described above, it is repeated that the mask (sample) 4 is scanned in a direction at almost right angles to a direction of a straight line, in which the plural elements of the CCD sensor 14 of the CCD camera 12 are arranged, a scanned amount at that time is measured by means of the laser measuring instrument 23, and an electric charge is transferred to plural elements in an adjacent line of the plural elements of the CCD sensor 14 detecting an image of the mask (sample) 4 synchronously with a moving amount of the mask (sample) 4, so that a delay type of integration would be performed to produce an image with high quality, while a moving and shifting amount at right angles to a direction of scan of the mask (sample) 4 is measured by means of the laser measuring instrument 23 and the deflector 8 is supplied with a compensation voltage or a compensation current to correct a line of the scan, so that it would be possible to produce an image scanned in a straight line with the extremely high accuracy without zigzag scan even when a stage with an easy structure is used.

Figure 12:
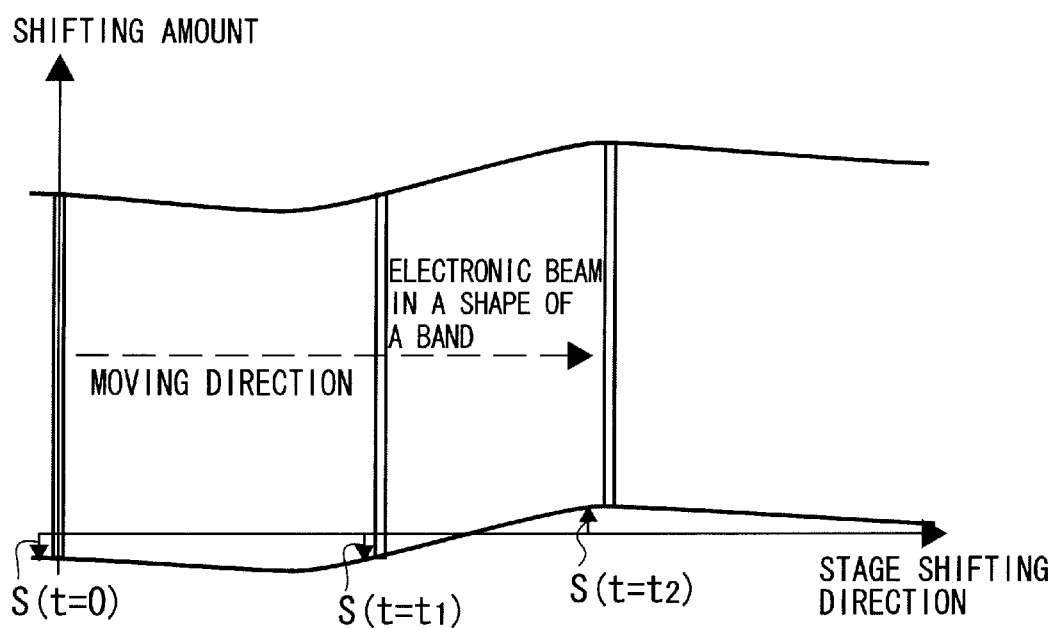
FIG. 12 is a diagram illustrating the invention.

FIG. 12 is a diagram illustrating the invention. In FIG. 12, a horizontal axis denotes a shifting direction (a scanning direction) of the stage 5 shown in FIGS. 10 and 11, while a vertical axis denotes a shifting amount (a moving and shifting amount) in a direction of right angles in scanning the stage.

In FIG. 12, the stage 5 on which the mask (sample) 4 is mounted is moved in a direction of almost right angles to a straight line, in which the plural elements of the CCD sensor 14 are arranged, as a stage shifting direction shown in the drawings. At this time, when respective shifting amounts at a time t=0, t1 and t2 are measured to be S (t=0), S (t=t1) and S (t=t2), respectively, by means of the laser measuring instrument 23 shown in FIG. 11, the deflector 8 is supplied with a corresponding electric voltage or current in order to correct the above shifting amounts S (t=0), S (t=t1) and S (t=t2), and as a result, the shifting amount can be arranged to be nothing in the plural elements of the CCD sensor 14. Accordingly, even when a line of the scan is zigzag a little due to an easy structure of the stage 5, the zigzag (a shifting amount in FIG. 12) can be measured by means of the laser measuring instrument 23 so as to be corrected by the deflector 8, and as a result, an image scanned accurately in a straight line can be produced.

The mask (sample) 4 is put on the movable stage 5 to be illuminated by an electronic beam and moved on the stage 5 at almost right angles to a direction of the plural elements of the CCD sensor 14. The CCD sensor 14 is a two-dimensional arrangement type of CCD, and each element can transfer an electric charge in any of vertical and horizontal directions in arrangement synchronously with a synchronization signal. An image formed after transmitting through or reflecting at the mask (sample) 4 in accordance with movement of the stage 5 moves on the CCD sensor 14. Following to the movement of the image, an electric charge of each element of the CCD sensor 14 is transferred in a direction of the movement (time delay integration is performed). Accumulation of an electric charge starts at a time when a point of an electronic image enters into a detecting element of the CCD sensor 14, and continues until the point moves outside the detecting element. As a result, the mask (sample) 4 is continuously moved without stopping the stage 5, while strength of a detecting signal can be increases. Furthermore, detection is carried out in each element arranged in the CCD sensor 14 at the same time in the same way, so that it becomes possible to carry out parallel detection as many as the number of the arranged elements (4096 elements in a line, for example), and thereby, an image can be detected at much higher speed.

INDUSTRIAL APPLICABILITY

As described above, the invention adopts a structure that an electronic beam transmitting through a mask 1 is detected by means of a detector, in which a plurality of elements is arranged in a plurality of lines, and an image signal (an electric charge) is transferred one by one by the detector synchronously with movement of the mask 1. Thus, the invention would be suitable to effectively utilize high resolution due to a short wavelength of the electronic beam as well as transfer an image signal (an electric charge) at right angles to a line of the detector synchronously with same time detection of pixels in a direction of the line so as to inspect the mask with high resolution at high speed.

Moreover, the invention adopts a structure that an electronic beam illuminates a sample (mask) while the sample is scanned in a straight line at right angles to a direction of plural elements of the CCD sensor and a moving and shifting amount in a direction at right angles to a direction of the scan is detected to correct an electronic beam by deflection or by movement by means of a sample moving mechanism. Thus, the invention is suitable to scan the sample (mask) in a straight line with extremely high accuracy with respect to an electronic beam so as to produce an image scanned in a straight line with extremely high accuracy without zigzag scan even when a stage with an easy structure is used.

FIG. 1
1: EMITTER
1: MASK
2: STAGE
3: ELECTRON GUN
4: CONDENSER LENS
5: OBJECTIVE LENS
6: PROJECTIVE LENS
7: TRANSDUCER
8: CAMERA LENS
9: CCD
12: MOTOR
13: VACUUM CHAMBER
15: CONTROLLING DEVICE
FIG. 2
101: LINE (4096 ELEMENTS)
103: OPTICAL IMAGE
104: OPTICAL IMAGE
105: PATTERN
106: PATTERN
MOVE
FIG. 3
21: MASK INSPECTION APPARATUS
25: CCD CAMERA
1: MASK
2: STAGE
12: MOTOR
SYNCHRONIZATION SIGNAL
LOCATION SIGNAL
MOTOR DRIVING
15: CONTROLLING DEVICE
18: IMAGE MEMORY
16: LOCATION CONTROLLING DEVICE
17: STAGE POWER SUPPLY
FIG. 4
(B)
[STEP MOVEMENT ®
   CONTINUOUS MOVEMENT-⁻]
FIG. 5

| ITEM | PRESENT INVENTION | RELATED ART |
|---|---|---|
| DETECTING SENSITIVITY | 30 nm | 50 nm |
| EFFECTIVE SAMPLING RATE | 200 MHz | 7.9 MHz |
| SCANNING TIME PER 1 cm$^2$ | 12 MINUTES | 3 HOURS AND 30 MINUTES |
| BEAM CURRENT DENSITY | 7 mA/cm2 | 56 A/cm$^2$ |
| BEAM DEFLECTION | UNNECESSARY | NECESSARY |

FIG. 6
1: MASK
2: STAGE
3: ELECTRON GUN
5: OBJECTIVE LENS
6: PROJECTIVE LENS
9': CCD SENSOR
11: EMITTER
12: MOTOR
13: VACUUM CHAMBER
15: CONTROLLING DEVICE
26: SIGNAL PROCESSING APPARATUS
FIG. 7
1: MASK
2: STAGE
3: ELECTRON GUN
5: OBJECTIVE LENS
6: PROJECTIVE LENS
9': CCD SENSOR
11: EMITTER
12: MOTOR
13: VACUUM CHAMBER
15: CONTROLLING DEVICE
26: SIGNAL PROCESSING APPARATUS
27: FLUORESCENT SCREEN
28: MONITORING WINDOW
29: LENS
30: CCD CAMERA
FIG. 8
1: MASK
2: STAGE
3: ELECTRON GUN
5: OBJECTIVE LENS
6: PROJECTIVE LENS
9': CCD SENSOR
11: EMITTER
12: MOTOR
13: VACUUM CHAMBER
15: CONTROLLING DEVICE
26: SIGNAL PROCESSING APPARATUS
27: FLUORESCENT SCREEN
28: MONITORING WINDOW
29: LENS
30: CCD CAMERA
31: LASER INTERFERENCE MEASURING INSTRUMENT
32: MIRROR
FIG. 9
(A)
FLUORESCENT BODY (APPLIED)

OPTICAL FIBER
CCD
(B)
FLUORESCENT BODY (APPLIED)
OPTICAL FIBER
CCD
FIG. 10
1: ELECTRON GUN
2: EMITTER
3: FOCUSING LENS
4: MASK
5: STAGE
6: OBJECTIVE LENS
7: VACUUM CHAMBER
8: DEFLECTOR
9: PROJECTIVE LENS
10: FLUORESCENT SCREEN
11: MONITORING WINDOW
12: CCD CAMERA
13: LENS
14: CCD SENSOR
15: SIGNAL PROCESSING APPARATUS
16: CONTROLLING DEVICE
17: MOTOR
FIG. 11
W: AMOUNT OF DEFLECTION
4: MASK
5: STAGE
6: OBJECTIVE LENS
8: DEFLECTOR
9: PROJECTIVE LENS
9-1: MIDDLE LENS
10: FLUORESCENT SCREEN
21: ELECTRONIC BEAM
22: DEFLECTION POWER SUPPLY
23: LASER MEASURING INSTRUMENT
24: LOCATION CONTROLLING DEVICE
25: STAGE POWER SUPPLY
FIG. 12
[FROM THE TOP TO THE BOTTOM]
SHIFTING AMOUNT
ELECTRONIC BEAM IN A SHAPE OF A BAND
MOVING DIRECTION
S (T=0)
S (T=T1)
S (T=T2)
STAGE SHIFTING DIRECTION

What is claimed is:

1. A mask inspection apparatus for performing a transmission type of inspection of a mask, characterized by comprising:

an electron gun for emitting an electronic beam;

a lens for enabling the electronic beam emitted from the above electron gun to illuminate the above mask;

a lens for forming into an image the electronic beam having transmitted through the above mask;

a detector for detecting an image of the electronic beam formed by the above lens or an image obtained after the above image of the electronic beam has been transduced into light, and for transferring an image signal at right angles to a line, the detector having a plurality of pixels aligned in a direction of the line and a plurality of the lines;

moving means for moving the above mask; and controlling means for controlling the above image signal in the detector to be transferred synchronously when the moving means moves the above mask.

2. The mask inspection apparatus according to claim 1, characterized in that it is repeated to move the above mask by the above moving means at a predetermined width in a certain direction or in a direction adverse to the certain direction so as to scan a whole surface of the above mask.

3. The mask inspection apparatus according to claim 1, characterized in that the above moving means continuously moves the above mask.

4. The mask inspection apparatus according to claim 1, characterized in that the above image of the electronic beam is transduced into light by a transducer before the image is formed on the above detector by means of an optical lens.

5. The mask inspection apparatus according to claim 1, characterized in that an amount of an X ray is reduced by disposing before the detector a board, which cuts off the X ray and through which an optical image passes, or by forming on the above detector an optical image, which is transduced from the image of the electronic beam by an electronic beam-light transducer disposed obliquely, by means of a lens.

6. The mask inspection apparatus according to claim 1, characterized in that a location of the mask fixed on a sample table is measured by means of a laser interference measuring instrument so that the above mask would be moved.

7. The mask inspection apparatus according to claim 1, characterized in that the above image of the electronic beam is formed on a surface, which is formed by flatting one sectional surface of a number of fibers bundled and to which a fluorescent body for transducing an electron into light is applied, and that a detector is disposed on the other sectional surface flatted.

8. The mask inspection apparatus according to claim 7, characterized in that the middle of the fiber is cut so that the section would be flatted and the cut fiber is interconnected if necessary to detect an image.

9. A mask inspection apparatus for producing an image of a mask at high speed, characterized by comprising:

electronic beam emitting means for emitting an electronic beam;

a lens for enabling the above emitted electronic beam to illuminate the mask;

a lens for forming into an image the electronic beam having transmitted through the above mask illuminated by the electronic beam or an electronic beam having reversed in the vicinity of a surface of the mask to which a minus voltage is applied;

a detector for detecting an image formed by the above lens by means of a plurality of pixels aligned in a straight line;

scanning means for scanning the above mask in a straight line so that the straight line would be at almost right angles to a direction that the above plurality of pixels are aligned in a straight line;

detecting means for detecting a moving and shifting amount at right angles to a direction of the above scan in scanning in a straight line by the above scanning means; and correcting means for outputting a controlling signal to a deflector or a moving mechanism of the mask for deflecting an image so as to correct the moving and shifting amount detected by the above detecting means.

10. The mask inspection apparatus according to claim 9, characterized in that a plurality of pixels is disposed as the above detector in a straight line with respect to the above formed image so as to form a detector, in which an electric charge is transferred and accumulated synchronously with the above scan of an electronic beam at right angles adjacent to the above plurality of pixels disposed in a straight line and in which one or a plurality lines of a plurality pixels is provided in a straight line.

11. The mask inspection apparatus according to claim 9, characterized in that a detector comprising a plurality of detecting elements in a straight line for detecting an electronic image directly, or a detector comprising a plurality of detecting elements in a straight line for forming and detecting an optical image having been transduced from an electronic image is used as the above detector.

12. The mask inspection apparatus according to claim 9, characterized by comprising a rotating device for making a direction of the above scan almost same at right angles to the plurality of pixels in a straight line of the above detector.

13. The mask inspection apparatus according to claim 9, characterized in that an electronic beam is formed into a shape of a band so as not to illuminate unnecessary part of the mask.

\* \* \* \* \*

UNITED STATES PATENT AND TRADEMARK OFFICE
CERTIFICATE OF CORRECTION

PATENT NO. : 6,686,591 B2
DATED : February 3, 2004
INVENTOR(S) : Minoru Ito et al.

It is certified that error appears in the above-identified patent and that said Letters Patent is hereby corrected as shown below:

Title page,
Item [54], Title, change "APPARATUS FOR INSPECTING MASK" to -- MASK INSPECTION APPARATUS --
Item [57], ABSTRACT,
Line 2, after "by" insert -- means of --

Signed and Sealed this

Eighteenth Day of May, 2004

JON W. DUDAS
*Acting Director of the United States Patent and Trademark Office*